United States Patent [19]

Rebre et al.

[11] Patent Number: 5,412,037
[45] Date of Patent: May 2, 1995

[54] SUPERABSORBENT ACRYLIC POWDERS

[75] Inventors: Shu R. Rebre, Vincennes; Christian Collette, Paris; André Kowalik, Gouvieux, all of France

[73] Assignee: Elf Atochem S.A., Puteaux, France

[21] Appl. No.: 293,031

[22] Filed: Aug. 19, 1994

Related U.S. Application Data

[62] Division of Ser. No. 104,761, Aug. 12, 1993.

[30] Foreign Application Priority Data

Aug. 12, 1993 [FR] France ................... 92 09960

[51] Int. Cl.⁶ .......................................... C08F 265/02
[52] U.S. Cl. .................................. 525/301; 525/256; 525/268
[58] Field of Search .................... 525/301, 256, 268

[56] References Cited

U.S. PATENT DOCUMENTS

| | | | |
|---|---|---|---|
| 4,745,154 | 5/1988 | Ruffner | 524/801 |
| 4,783,510 | 11/1988 | Saotome | 525/329.7 |

FOREIGN PATENT DOCUMENTS 0441507  8/1991  European Pat. Off. .

*Primary Examiner*—Vasu S. Jagannathan
*Attorney, Agent, or Firm*—Burns, Doane, Swecker & Mathis

[57] ABSTRACT

Particulates of a superabsorbent partially, neutralized acrylic polymer, e.g., polyacrylic acid, having a mean particle size ranging from 100 to 500 μm, essentially monodisperse and essentially devoid of fines having a particle size of less than 100 μm, having a nonuniformly surfaced spheroidal particle morphology and well suited for a variety of hygienic applications, are prepared by (i) polymerizing a suspension of an acrylic monomer charge I in an organic medium and producing a suspension of acrylic polymer gel particles, such acrylic monomer charge I having a degree of neutralization greater than that desired in the final superabsorbent polymer, (ii) next absorbing a second acrylic monomer charge II into the gel particles, such acrylic monomer charge II having a degree of neutralization less than that desired in the final superabsorbent polymer, and (iii) polymerizing in the gel particles the second acrylic monomer charge II.

5 Claims, 1 Drawing Sheet

SUPERABSORBENT ACRYLIC POWDERS

CROSS-REFERENCE TO COMPANION APPLICATIONS

This application is a divisional of application Ser. No. 08/104,761, filed Aug. 12, 1993, and is related to our applications Ser. Nos. 08/104,757, now U.S. Pat. No. 5,373,066 [Attorney Docket No. 006050-318] and 08/104,756 (pending) [Attorney Docket No. 006050-320], both filed concurrently herewith and incorporated by reference herein, and assigned to the assignee hereof.

BACKGROUND OF THE INVENTION

1. Field of the Invention

The present invention relates to the production of superabsorbent acrylic polymer powders capable of absorbing large amounts of water or aqueous fluids and which are well suited for a variety of hygienic applications.

2. Description of the prior Art

It is known to this art to produce polymer particulates having a high capacity for water absorption by inverse suspension polymerization of ethylenically unsaturated monomers, more particularly of acrylic monomers. The powders which are thus obtained swell greatly in the presence of water, providing gels of high mechanical strength. These properties are useful, inter alia, for the manufacture of sanitary appliances, e.g., sanitary napkins, for absorption and retention of body fluids.

One significant improvement in the production of such absorbent powders is described in EP-0,441,507, comprising polymerization of the acrylic monomer in at least two separate stages. In a first discrete stage, an inverse suspension polymerization is carried out in conventional manner, such polymerization resulting in the formation of a gel. In a second stage, a fresh monomer charge is absorbed into this gel and polymerization thereof is initiated within the actual gel formed previously. If appropriate, this absorption/polymerization sequence can be repeated. In this fashion, polymeric resins are prepared having a particle size which is appreciably larger than the resins obtained via single inverse suspension polymerization. Their degree or extent of swelling in the presence of water, elastic modulus, plasticity and resistance to collapse under pressure of the gel, are also appreciably improved.

The absorbent properties of the final polymer depend on the degree of neutralization of the monomeric acrylic acid; it is now well known to this art that, for hygienic applications, the optimum degree of neutralization must be close to 75%, in particular taking account of the required compatibility of the superabsorbent with human skin. Thus, in the multistage process, a first inverse suspension polymerization of a first aqueous charge of 75% neutralized acrylic acid is conducted, and subsequent charges of aqueous acrylic acid, also 75% neutralized, are absorbed by the gel thus formed.

SUMMARY OF THE INVENTION

It has now unexpectedly been determined that, for the two-stage preparation of an about 75% neutralized superabsorbent acrylic polymer, for example, it is not required that each of the respective starting monomer solutions exhibits the same about 75% degree of neutralization; rather, monomer solutions can be used having varying degrees of neutralization, provided that the degree of neutralization of the final polymer remains at about 75%.

Briefly, the present invention features a two-stage process for the preparation of a superabsorbent acrylic polymer having a given degree of neutralization, comprising suspension polymerizing a first acrylic monomer charge exhibiting a degree of neutralization greater than that desired in the final polymer to form a gel therefrom, then absorbing into said gel a second acrylic monomer charge exhibiting a degree of neutralization less than that desired in the final polymer, and, finally, polymerizing said absorbed second monomer charge.

DETAILED DESCRIPTION OF PREFERRED EMBODIMENTS OF THE INVENTION

More particularly according to the present invention, to prepare an about 75% neutralized superabsorbent acrylic polymer, the first acrylic monomer charge characteristically exhibits a degree of neutralization ranging from about 90% to 100% and the second acrylic monomer charge exhibits a degree of neutralization ranging from about 60% to 50%.

Figure 1:
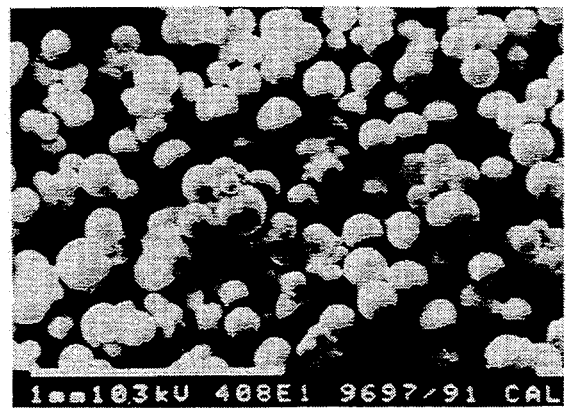
FIG. 1 is a photomicrograph showing superabsorbent acrylic polymer particles prepared according to the two-stage process of the prior art.
Figure 2:
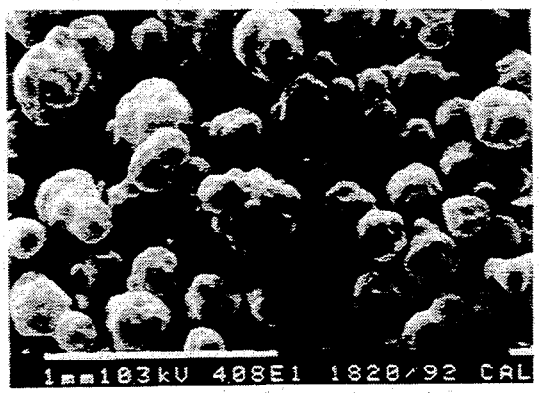
FIG. 2 is a photomicrograph showing superabsorbent acrylic polymer particles prepared according to the two-stage process of the present invention.

Surprisingly, the polymer particulates prepared according to the process of the present invention are not spherical in shape and morphology, as are those of the prior art (see FIG. 1), but are lumpy and spheriodal, resembling the shapes of truffles (see FIG. 2).

Moreover, the particle sizes of the polymer particulates according to this invention are substantially larger than those of the prior art, and range from about 100 to 500 μm, with a greatly reduced proportion or fraction of particulates (undersize) having a particle size less than 100 μm. It is of great advantage to directly produce large particles which are the only type that can be employed for the typical applications, since this permits avoiding or limiting a postagglomeration sequence. Particles of this size are known to the art, but are produced only from decreased monomer charges; this has an adverse effect on the yield of the operation, and the particles which are thus obtained are excessively polydisperse.

The process according to the invention not only economically provides large particles, but also an essentially monodisperse narrower particle size distribution.

Moreover, the nonuniform geometry of the particles permits a better binding into a fibrous matrix or medium and, hence, greater ease of processing in the production, e.g., of sanitary napkins.

The suspension polymerization is advantageously carried out in the presence of an effective amount of a surfactant. The surfactants which can thus be employed are the surfactants known for such purpose in the prior art, in particular the nonionic surfactants such as the fatty acid esters of sorbitan, of polyglycerine and of sucrose, or polyoxyethylene alkylphenyl ethers.

However, it is also conspicuously advantageous to formulate the inverse suspension of the first monomer charge using surfactants of polyethylene glycol/dodecyl glycol block copolymer type which comprise a polyethylene glycol backbone provided at either or both ends of the polymer with a number of hydrophobic endgroups comprising dodecyl glycol residues. The absorption of the second monomer charge by the polymer gel formed initially can then be accomplished without the need for cooling the reactor extensively and this absorption stage can be carried out at temperatures which are not less than 35° C., thereby very appreciably improving the profitability of the process.

It is also possible to employ surfactants of polymerizable type, corresponding to the general formula:

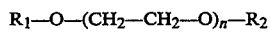

$$R_1\text{—O—}(CH_2\text{—}CH_2\text{—O})_n\text{—}R_2$$

wherein $R_1$ is a hydrocarbon having at least 9 carbon atoms; $R_2$ is a polymerizable functional group or an acryloyl, methacryloyl or maleoyl radical; and the degree of condensation n of the ethylene oxide ranges from 30 to 70. Using such surfactants, the stage of absorption of the second monomer charge may be conducted at a temperature of about 45° C. The maleic monoester of nonylphenol, oxyethylenated with 50 molecules of ethylene oxide, is a preferred surfactant of this type.

In order to further illustrate the present invention and the advantages thereof, the following specific examples are given, it being understood that same are intended only as illustrative and in nowise limitative.

In said examples, the following sequences are distinguished:

(a) formulation of the solvent phase;
(b) preparation of the aqueous monomer phase (charge I);
(c) placing the monomer in suspension and polymerization I;
(d) preparation of the aqueous monomer phase (charge II);
(e) absorption of the charge II and polymerization II; and
(f) isolation of the polymer thus produced.

EXAMPLE 1 (Comparative)

The example corresponds to a two-stage preparation according to the prior art of a 75% neutralized polyacrylate by successive use of acrylic acid solutions, both 75% neutralized.

Sequence(a):

0.92 g of polyethylene modified with maleic anhydride, marketed by Mitsui Petrochemical Industries under the trademark Hi-Wax 1105A, used as a protective colloid, and 0.736 g of sucrose di/tristearate were dissolved in 376 g of heptane at 80° C. and under stirring at 400 revolutions/minute in a one-liter reactor fitted with means for introducing solid or liquid reactants, a stirrer, a system for purging with neutral gas, a temperature probe and a heating/refrigerating device. The mixture was cooled to 38° C.

Sequence (b):

Separately, 92 g of an aqueous solution containing 80% by weight of acrylic acid were neutralized with 176.8 g of 17.35% soda lye. Then, 0.276 g of hydroxyethyl cellulose was added, followed by 5.5 g of an aqueous solution containing 1% of potassium persulfate and 0.92 g of an aqueous solution containing 2% of ethylene glycol diglycidyl ether. This operation was carried out at a temperature of approximately 15° C.

Sequence (c):

With the reactor being stirred at 400 revolutions/minute and with nitrogen purging at a rate of 80 liters/minute, the aqueous phase prepared previously, which converted into inverse suspension in heptane, was introduced therein small amounts at a time. The temperature was increased to 70° C. to induce polymerization; it was maintained at this value for 30 minutes. The reaction medium was then cooled to 20° C.

Sequence (d):

While the above procedure was being carried out, 92 g of aqueous solution containing 80% by weight of acrylic acid were separately neutralized with 176.8 g of 17.35% soda lye, followed by the addition of 5.5 g of an aqueous solution containing 1% of potassium persulfate and 0.92 g of an aqueous solution containing 2% of ethylene glycol diglycidyl ether. The preparation of this aqueous phase, which constituted the monomer charge II, was conducted at a temperature of approximately 15° C.

Sequence (e):

The stirring in the reactor was increased to 800 revolutions/minute, the nitrogen purging being maintained at 80 liters/minute. The charge II was introduced therein small amounts at a time, after which the temperature was increased to 70° C. to initiate the second stage of polymerization. The polymerization was permitted to proceed for one-half hour.

Final sequence (f):

The heptane and most of the water were removed by distillation. Then, 9.2 g of an aqueous solution containing 2% of ethylene glycol diglycidyl ether were added to the contents of the reactor and drying was continued.

A powder comprising spherical particles (FIG. 1), the undersize of which, at 100 μm, attained a value of 1% was thus obtained; a photomicrograph of such powder is shown in FIG. 1.

EXAMPLE 2

In this example, in accordance with the invention, a polyacrylate having a degree of neutralization of 75% was produced by using a first solution of 100% neutralized acrylic acid, followed by absorption/polymerization of a second solution, 50% neutralized.

The procedure of Example 1 was repeated, except that in sequence (b) the 92 g of 80% polyacrylic acid were neutralized with 176.8 g of 23.13% soda lye and that in sequence (d) the 92 g of 80% polyacrylic acid were neutralized with 177.7 g of 11.56% soda lye.

A powder comprised of nonuniform spheroids (FIG. 2) was thus obtained, having a narrow particle size distribution, the undersize of which at 100 μm was essentially zero; a photomicrograph of such powder is shown in FIG. 2.

EXAMPLE 3

In this example, the advantage of the combination of an overneutralization of the first monomer charge and of an underneutralization of the second charge was combined with the use of a polyethylene glycol/dodecyl glycol block copolymer, Dapral E348, marketed by AKZO (molecule containing approximately three dodecyl glycol residues with one end group of a methoxypolyethylene glycol polymer chain containing approximately 22 ethylene glycol recurring structured units), by virtue of which the absorption of the second monomer charge by the gel formed during the first polymerization was carried out at the relatively high temperature of 35° C.

The essential differences in the operating procedure, when compared with Example 1, are reported below:

Sequence (a):

The organic phase comprised 285.1 g of heptane, 0.92 g of polyethylene modified with maleic anhydride, a product marketed by Mitsui Petrochemical Industries under the trademark Hi-Wax 1105A and 0.46 g of Dapral E348;

Sequence (b):

Charge I included 92 g of an aqueous solution containing 80% by weight of acrylic acid, 160.65 g of 24.17% soda lye, 2.75 g of an aqueous solution containing 2% of potassium persulfate and 0.92% of an aqueous solution containing 2% of ethylene glycol diglycidyl ether.

Sequence (c):

After polymerization, the temperature of the contents of the reactor was adjusted to 36° C.

Sequence (d):

Charge II included 92 g of an aqueous solution containing 80% by weight of acrylic acid, 135.75 of 16.6% soda lye, 2.75 g of an aqueous solution containing 2% of potassium persulfate and 0.92 g of an aqueous solution containing 2% of ethylene glycol diglycidyl ether, cooled to a temperature of 15° C. before use in the next sequence.

A powder was thus obtained, comprising spheroids having a nonuniform surface without appreciable undersize at 100 μm, via the subject process, the economics of which were very appreciably improved in comparison with those of the prior art which require a substantial cooling of the reactor in order to permit the sequence (d).

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. Particulates of a superabsorbent partially neutralized acrylic polymer, having a mean particle size ranging from 100 to 500 μm, essentially monodisperse and essentially devoid of fines having a particle size of less than 100 μm, and having a nonuniformly surfaced spheroidal particle morphology.

2. The superabsorbent particulates as defined by claim 1, comprising partially neutralized polyacrylic acid.

3. The superabsorbent particulates as defined by claim 2, comprising from 65% to 85% neutralized polyacrylic acid.

4. The superabsorbent particulates as defined by claim 3, comprising about 75% neutralized polyacrylic acid.

5. The superabsorbent particulates as defined by claim 1, having the morphology shown in FIG. 2.

* * * * *